United States Patent
Alcaraz et al.

(10) Patent No.: US 6,949,539 B2
(45) Date of Patent: Sep. 27, 2005

(54) ADMANTANE DERIVATIVES

(75) Inventors: Lilian Alcaraz, Loughborough (GB); Mark Furber, Loughborough (GB)

(73) Assignee: AstraZeneca AB, Södertälje (SE)

(*) Notice: Subject to any disclaimer, the term of this patent is extended or adjusted under 35 U.S.C. 154(b) by 72 days.

(21) Appl. No.: 10/297,486

(22) PCT Filed: Jun. 1, 2001

(86) PCT No.: PCT/SE01/01257

§ 371 (c)(1),
(2), (4) Date: Dec. 6, 2002

(87) PCT Pub. No.: WO01/94338

PCT Pub. Date: Dec. 13, 2001

(65) Prior Publication Data

US 2003/0187031 A1 Oct. 2, 2003

(51) Int. Cl.[7] ................. A61K 31/44; C07D 213/02
(52) U.S. Cl. ............. 514/211.08; 514/216; 514/230.5; 514/235.5; 514/253.01; 514/253.13; 514/300; 514/305; 514/318; 514/337; 514/338; 514/339; 514/340; 514/341; 514/343; 514/346; 514/352; 514/354; 540/575; 540/582; 544/74; 544/130; 544/360; 544/365; 546/122; 546/133; 546/137; 546/194; 546/276.4; 546/276.7; 546/279.1; 546/291; 546/292; 546/207; 546/298; 546/308; 546/309; 546/323
(58) Field of Search ................. 544/365; 540/575; 546/194, 279.1, 323; 514/253.13, 211.08, 318, 343, 354

(56) References Cited

U.S. PATENT DOCUMENTS

| | | | |
|---|---|---|---|
| 3,464,998 A | 9/1969 | Krimmel | 260/295.5 |
| 3,471,491 A | 10/1969 | Venkatachala et al. | 260/249.9 |
| 4,751,292 A | 6/1988 | Fox | 536/24 |

FOREIGN PATENT DOCUMENTS

| | | | | |
|---|---|---|---|---|
| BE | 650919 A | 7/1964 | | |
| DE | 1943404 A | 12/1970 | | |
| EP | 0002065 A1 | 5/1979 | | |
| EP | 0867436 A1 | 9/1998 | | |
| WO | WO 95/04720 | 2/1995 | | |
| WO | WO 99/29660 | 6/1999 | | |
| WO | WO 9929660 A1 * | 6/1999 | ......... | C07C/233/25 |
| WO | WO 99/29661 | 6/1999 | | |
| WO | WO 9929661 A1 * | 6/1999 | ......... | C07C/233/65 |
| WO | WO 00/61569 | 10/2000 | | |
| WO | WO 03/041707 | 5/2003 | | |
| WO | WO 03/080579 | 10/2003 | | |

OTHER PUBLICATIONS

Costakis et al., "Synthesis of Some Adamantane Derivatives of 2-Aminobenzothiazoles", *Journal of Medicinal Chemistry* 14(12):1222–1223 (1971).

Ho et al., "Synthesis of a Peptidomimetic Tricyclic Tetrahydrobenzo[*ij*] quinoline as a VLA–4 Antagonist", *J. Org. Chem.* 65:6743–6748, p. 6745, scheme 5, (27) (2000).

STN International, File REGISTRY, see RN 405068–97–5, 405070–41–9, 405076–22–4, Apr. 14, 2002.

STN International, File REGISTRY, see RN 445032–09–7, Aug. 30, 2002.

STN International, File CHEMCATS, Accession No. 2001:48444, May 14, 2001, NS18552, 2-Quinolinecarboxamide, N–(tricycle[3.3.1.13,7]dec–1–ylmethyl), CAS Registry No. 313688–07–2.

STN International, File REGISTRY, see RN 401622–10–4, Mar. 24, 2002.

\* cited by examiner

*Primary Examiner*—Richard L. Raymond
(74) *Attorney, Agent, or Firm*—Fish & Richardson P.C.

(57) ABSTRACT

The invention provides compounds of general formula (I) in which m, A, R[1] and Ar have the meanings defined in the specification; a process for their preparation; pharmaceutical compositions containing them; a process for preparing the pharmaceutical compositions; and their use in therapy.

14 Claims, No Drawings

ADMANTANE DERIVATIVES

CROSS REFERENCE TO RELATED APPLICATIONS

The present application is a national phase application under 35 U.S.C Section 371 filed from International Patent Application PCT/SE01/01257, filed 1 Jun. 2001, which claims priority to United Kingdom patent application Serial No. 0013737.2, filed 7 Jun. 2000. The contents of these applications are incorporated herein by reference in their entirety.

The present invention relates to adamantane derivatives, a process for their preparation, pharmaceutical compositions containing them, a process for preparing the pharmaceutical compositions, and their use in therapy.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and proliferation (T cells), apoptosis and L-selectin shedding (lymphocytes). $P2X_7$ receptors are also located on antigen-presenting cells (APC), keratinocytes, salivary acinar cells (parotid cells), hepatocytes and mesangial cells.

It would be desirable to make compounds effective as $P2X_7$ receptor antagonists for use in the treatment of inflammatory, immune or cardiovascular diseases, in the aetiologies of which the $P2X_7$ receptor may play a role.

In accordance with the present invention, there is therefore provided a compound of general formula

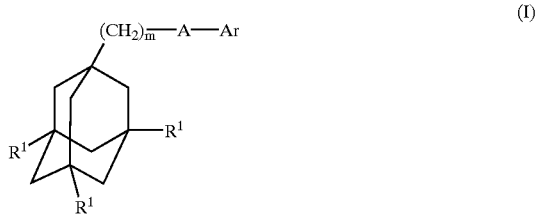

(I)

wherein m represents 1, 2 or 3, preferably 1 or 2;
each $R^1$ independently represents a hydrogen or halogen (e.g. fluorine, chlorine, bromine or iodine) atom, preferably a hydrogen atom;
A represents C(O)NH or, preferably, NHC(O);
Ar represents a group

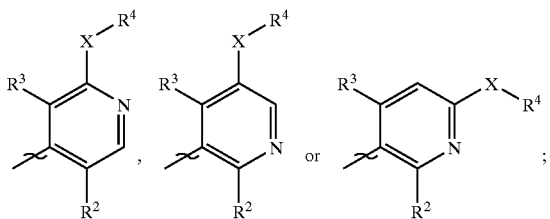

X represents a bond, an oxygen atom or a group $(CH_2)_{1-6}$, CH=, $(CH_2)_{1-6}O$, $O(CH_2)_{1-6}$, $O(CH_2)_{2-6}O$, $O(CH_2)_{2-3}O(CH_2)_{1-3}$, $(CH_2)_{1-3}O(CH_2)_{1-3}$, $(CH_2)_{1-3}O(CH_2)_{2-3}O$, $NR^5$, $(CH_2)_{1-6}NR^5$, $NR^5(CH_2)_{1-6}$, $(CH_2)_{1-3}NR^5(CH_2)_{1-3}$, $O(CH_2)_{2-6}NR^5$, $O(CH_2)_{2-3}NR^5(CH_2)_{1-3}$, $(CH_2)_{1-3}NR^5 (CH_2)_{2-3}O$, $NR^5(CH_2)_{2-6}O$, $NR^5(CH_2)_{2-3}O(CH_2)_{1-3}$;

one of $R^2$ and $R^3$ represents a halogen, cyano, nitro, amino, hydroxyl, or a group selected from (i) $C_1$–$C_6$ alkyl optionally substituted by at least one $C_3$–$C_6$ cycloalkyl, (ii) $C_3$–$C_8$ cycloalkyl, (iii) $C_1$–$C_6$ alkyloxy optionally substituted by at least one $C_3$–$C_6$ cycloalkyl, and (iv) $C_3$–$C_8$ cycloalkyloxy, each of these groups being optionally substituted by one or more fluorine atoms, and the other of $R^2$ and $R^3$ represents a hydrogen or halogen atom;
either $R^4$ represents a 3- to 9-membered saturated or unsaturated aliphatic heterocyclic ring system containing one or two nitrogen atoms and optionally an oxygen atom, the heterocyclic ring system being optionally substituted by one or more substituents independently selected from fluorine atoms, hydroxyl, carboxyl, cyano, $C_1$–$C_6$ alkyl, $C_1$–$C_6$ hydroxyalkyl, —$NR^6R^7$, —$(CH_2)_rNR^6R^7$ and —$CONR^6R^7$, or $R^4$ represents a 3- to 8-membered saturated carbocyclic ring system substituted by one or more substituents independently selected from —$NR^6R^7$, —$(CH_2)_rNR^6R^7$ and —$CONR^6R^7$, the ring system being optionally further substituted by one or more substituents independently selected from fluorine atoms, hydroxyl and $C_1$–$C_6$ alkyl;
r is 1,2,3,4,5 or 6;
$R^5$ represents a hydrogen atom or a $C_1$–$C_6$ alkyl or $C_3$–$C_8$ cycloalkyl group;
$R^6$ and $R^7$ each independently represent a hydrogen atom or a $C_1$–$C_6$ alkyl, $C_2$–$C_6$ hydroxyalkyl or $C_3$–$C_8$ cycloalkyl group, or $R^6$ and $R^7$ together with the nitrogen atom to which they are attached form a 3- to 8-membered saturated heterocyclic ring; with the provisos that,
(a) when A represents C(O)NH and $R^4$ represents an unsubstituted 3- to 8-membered saturated aliphatic heterocyclic ring system containing one nitrogen atom, then X is other than a bond, and
(b) when A represents C(O)NH and X represents a group $(CH_2)_{1-6}$ or $O(CH_2)_{1-6}$, then $R^4$ does not represent an unsubstituted imidazolyl, unsubstituted morpholinyl, unsubstituted piperidinyl or unsubstituted pyrrolidinyl group, and
(c) when A represents NHC(O) and $R^4$ represents an unsubstituted 3- to 8-membered saturated aliphatic heterocyclic ring system containing one nitrogen atom, then X is other than a bond, and
(d) when A represents NHC(O) and X represents $O(CH_2)_{1-6}$ or $NH(CH_2)_{1-6}$, then $R^4$ does not represent an unsubstituted 1-piperidinyl or unsubstituted 1-pyrrolidinyl group, and
(e) when A represents NHC(O) and X represents $O(CH_2)_{2-3}NH(CH_2)_2$, then $R^4$ does not represent an imidazolyl group;
or a pharmaceutically acceptable salt or solvate thereof.

In the context of the present specification, unless otherwise indicated, an alkyl substituent or alkyl moiety in a substituent group may be linear or branched. Examples of alkyl groups/moieties containing up to 6 carbon atoms include methyl, ethyl, propyl, isopropyl, butyl, isobutyl, tert-butyl, pentyl and hexyl. When one of $R^2$ and $R^3$ represents a $C_1$–$C_6$ alkyl/$C_1$–$C_6$ alkyloxy optionally substituted by at least one $C_3$–$C_6$ cycloalkyl, it should be understood that one or both of the alkyl and cycloalkyl moieties may be optionally substituted by fluorine atoms. In relation to $R^4$, a 3- to 9-membered saturated or unsaturated aliphatic heterocyclic ring system containing one or two nitrogen atoms and optionally an oxygen atom may be a monocyclic or bicyclic ring system. Also in relation to $R^4$, a 3- to 8-membered saturated carbocyclic ring system may be a monocyclic or bicyclic ring system. When $R^6$ or $R^7$ represents a $C_2$–$C_6$ hydroxyalkyl in the substituent $NR^6R^7$, —$(CH_2)_rNR^6R^7$ or —$CONR^6R^7$, it will be appreciated that the hydroxyl group will not be bonded to the same carbon atom as the nitrogen atom. When $R^6$ and $R^7$ together with the nitrogen atom to which they are attached form a 3- to 8-membered saturated heterocyclic ring, the ring obtained is monocyclic. A hydroxyalkyl substituent may contain one or more hydroxyl groups but preferably contains one hydroxyl group.

Preferably X represents a bond, an oxygen atom or a group $O(CH_2)_{1-6}$, $NR^5$ or $NR^5(CH_2)_{1-6}$.

One of $R^2$ and $R^3$ represents a halogen (e.g. fluorine, chlorine, bromine or iodine), cyano, nitro, amino, hydroxyl, or a group selected from (i) $C_1$–$C_6$ alkyl, preferably $C_1$–$C_4$ alkyl, optionally substituted by at least one (e.g. 1, 2 or 3) $C_3$–$C_6$ cycloalkyl (i.e. cyclopropyl, cyclobutyl, cyclopentyl or cyclohexyl), (ii) $C_3$–$C_8$ cycloalkyl (e.g. cyclopropyl, cyclobutyl, cyclopentyl or cyclohexyl), (iii) $C_1$–$C_6$ alkyloxy, preferably $C_1$–$C_4$ alkyloxy, optionally substituted by at least one (e.g. 1, 2 or 3) $C_3$–$C_6$ cycloalkyl (i.e. cyclopropyl, cyclobutyl, cyclopentyl or cyclohexyl), and (iv) $C_3$–$C_8$ cycloalkyloxy (e.g. cyclopropyloxy, cyclobutyloxy, cyclopentyloxy or cyclohexyloxy), each of these groups being optionally substituted by one or more (e.g. 1, 2, 3 or 4) fluorine atoms, and the other of $R^2$ and $R^3$ represents a hydrogen or halogen (e.g. fluorine, chlorine, bromine or iodine) atom.

Preferably, one of $R^2$ and $R^3$ represents a halogen (especially chlorine) atom and the other of $R^2$ and $R^3$ represents a hydrogen atom.

$R^4$ may represent a 3- to 9-membered saturated or unsaturated aliphatic heterocyclic ring system containing one or two nitrogen atoms and optionally an oxygen atom, the heterocyclic ring system being optionally substituted by one or more (e.g. 1, 2, 3 or 4) substituents independently selected from fluorine atoms, hydroxyl, carboxyl, cyano, $C_1$–$C_6$ alkyl, preferably $C_1$–$C_4$ alkyl, $C_1$–$C_6$ hydroxyalkyl, preferably $C_1$–$C_4$ hydroxyalkyl, —$NR^6R^7$, —$(CH_2)_rNR^6R^7$ and —$CONR^6R^7$.

The 3- to 9-membered saturated or unsaturated aliphatic heterocyclic ring system in the group $R^4$ may be a monocyclic ring system such as pyrrolidinyl (e.g. 1-pyrrolidinyl, 2-pyrrolidinyl or 3-pyrrolidinyl), piperidinyl (e.g. 1-piperidinyl, 2-piperidinyl, 3-piperidinyl or 4-piperidinyl), 4-piperiden-3-yl, piperazinyl (e.g. 1-piperazinyl), homopiperazinyl,

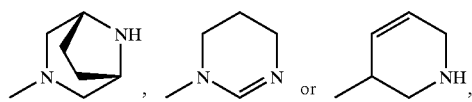

or a bicyclic ring system such as

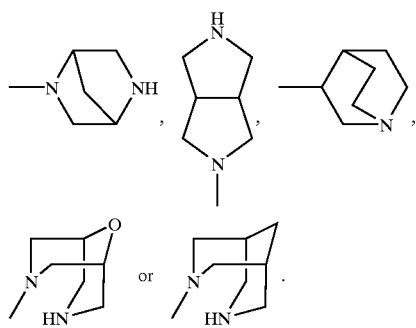

Alternatively, $R^4$ may represent a 3- to 8-membered saturated carbocyclic ring system substituted by one or more (e.g. 1, 2 or 3) substituents independently selected from $NR^6R^7$, —$(CH_2)_rNR^6R^7$ and —$CONR^6R^7$, the ring system being optionally further substituted by one or more (e.g. 1, 2, 3 or 4) substituents independently selected from fluorine atoms, hydroxyl and $C_1$–$C_6$ alkyl, preferably $C_1$–$C_4$ alkyl.

The 3- to 8-membered saturated carbocyclic ring in the group $R^4$ is preferably a monocyclic ring system such as a cyclopentyl or cyclohexyl ring.

Specific examples of groups $R^4$ include:

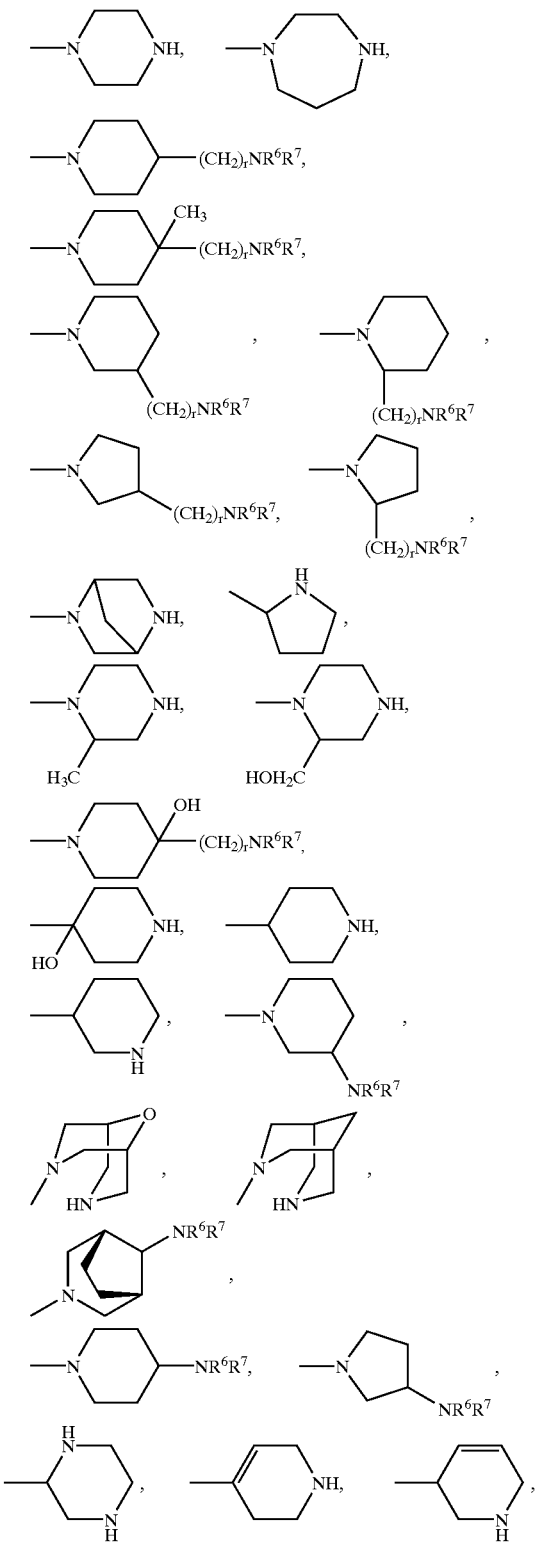

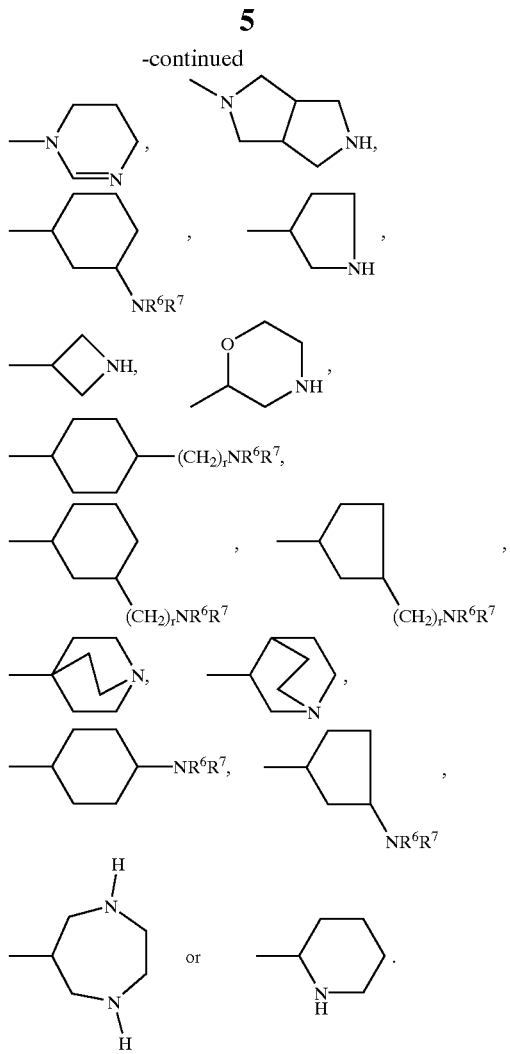

When X represents a bond or a group $(CH_2)_{1-6}$, $O(CH_2)_{2-6}$, $O(CH_2)_{2-3}O(CH_2)_{2-3}$, $(CH_2)_{1-3}O(CH_2)_{2-3}$, $NR^5(CH_2)_{2-6}$, $(CH_2)_{1-3}NR^5(CH_2)_{2-3}$, $O(CH_2)_{2-3}NR^5(CH_2)_{2-3}$ or $NR^5(CH_2)_{2-3}O(CH_2)_{2-3}$, $R^4$ preferably represents a group:

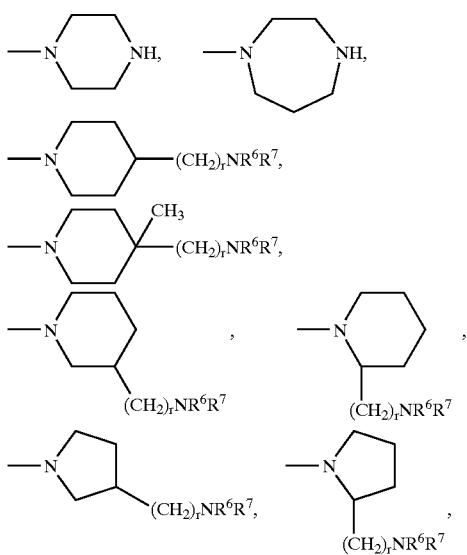

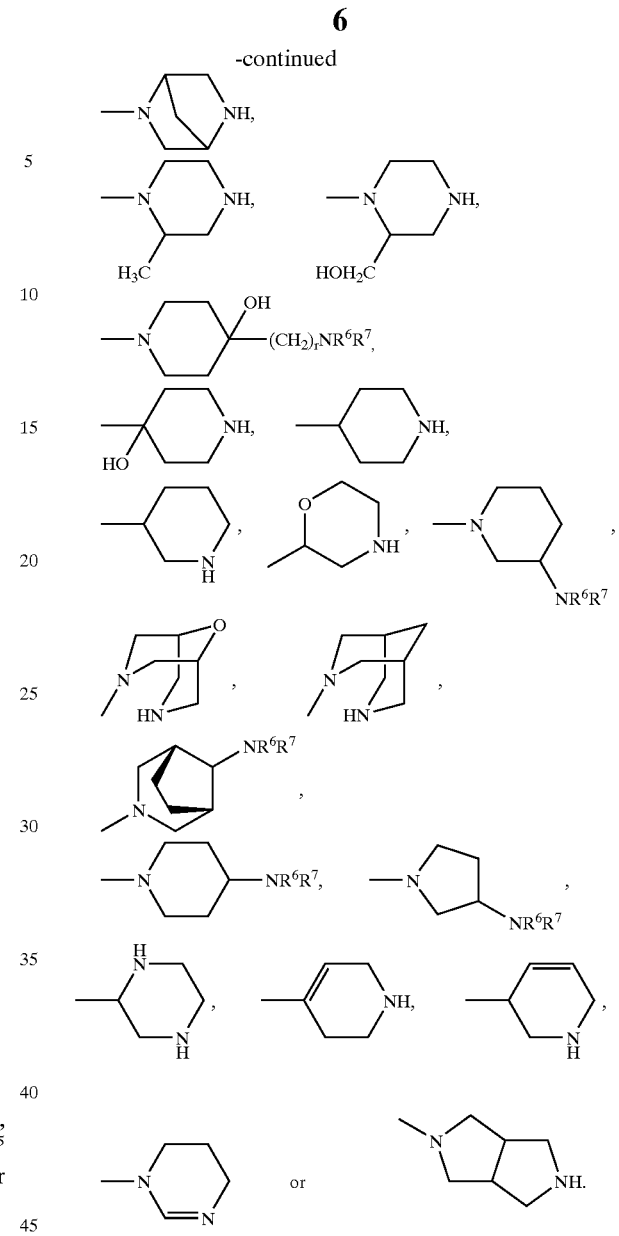

When X represents an oxygen atom or a group CH=, $(CH_2)_{1-6}O$, $OCH_2$, $O(CH_2)_{2-6}O$, $O(CH_2)_{2-3}OCH_2$, $(CH_2)_{1-3}OCH_2$, $(CH_2)_{1-3}O(CH_2)_{2-3}O$, $NR^5$, $(CH_2)_{1-6}NR^5$, $O(CH_2)_{2-6}NR^5$, $NR^5CH_2$, $(CH_2)_{1-3}NR^5CH_2$, $O(CH_2)_{2-3}NR^5CH_2$, $(CH_2)_{1-3}NR^5(CH_2)_{2-3}O$, $NR^5(CH_2)_{2-6}O$ or $NR^5(CH_2)_{2-3}OCH_2$, $R^4$ preferably represents a group:

-continued

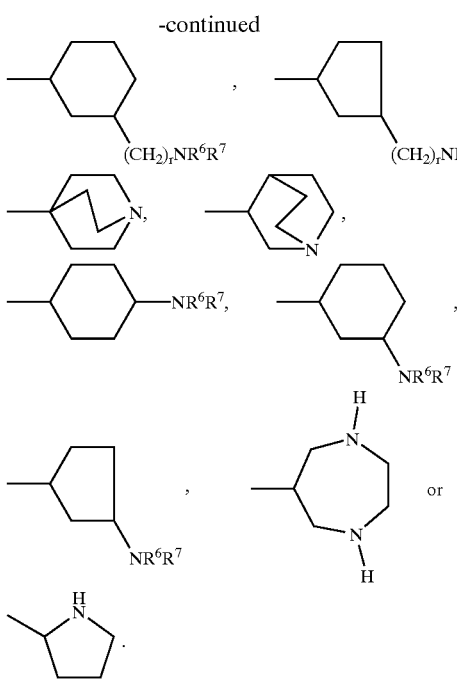

$R^5$ represents a hydrogen atom, or a $C_1$–$C_6$, preferably $C_1$–$C_4$, alkyl (e.g. methyl, ethyl, propyl, butyl, pentyl or hexyl) or $C_3$–$C_8$, preferably $C_3$–$C_6$, cycloalkyl (e.g. cyclopropyl, cyclobutyl, cyclopentyl or cyclohexyl) group. $R^5$ is especially a hydrogen atom.

$R^6$ and $R^7$ each independently represent a hydrogen atom, or a $C_1$–$C_6$, preferably $C_1$–$C_4$, alkyl (e.g. methyl, ethyl, propyl, butyl, pentyl or hexyl), $C_2$–$C_6$ hydroxyalkyl (e.g. hydroxymethyl or hydroxyethyl) or $C_3$–$C_8$, preferably $C_3$–$C_6$, cycloalkyl (e.g. cyclopropyl, cyclobutyl, cyclopentyl or cyclohexyl) group, or $R^6$ and $R^7$ together with the nitrogen atom to which they are attached form a 3- to 8-membered, preferably 3- to 6-membered, saturated heterocyclic ring such as a pyrrolidinyl or piperidinyl ring.

In the substituent —$NR^6R^7$, it is especially preferred that $R^6$ and $R^7$ both represent a hydrogen atom.

Preferred compounds of the invention include:

5-Chloro-2-piperazinyl-N-(tricyclo[3.3.1.1$^{3,7}$]dec-1-ylmethyl)-pyridine-4-carboxamide, hydrochloride salt, 5-Chloro-2-([1,4]-diazepan-1-yl)-N-(tricyclo[3.3.1.1$^{3,7}$]dec-1-ylmethyl)-pyridine-4-carboxamide, hydrochloride salt, 5-Chloro-2-(4-amino-piperidin-1-yl)-N-(tricyclo[3.3.1.1$^{3,7}$]dec-1-ylmethyl)-pyridine-4-carboxamide, hydrochloride salt, 5-Chloro-2-(4-piperidinylmethylamino)-N-(tricyclo[3.3.1.1$^{3,7}$]dec-1-ylmethyl)-pyridine-4-carboxamide, hydrochloride salt, 5-Chloro-2-(4-piperidinylmethylamino)-N-(tricyclo[3.3.1.1$^{3,7}$]dec-1-ylmethyl)-pyridine-4-carboxamide, hydrochloride salt, 5-Chloro-2-(3-aminopyrrolidin-1-yl)-N-(tricyclo[3.3.1.1$^{3,7}$]dec-1-ylmethyl)-pyridine-4-carboxamide, hydrochloride salt, 5-Chloro-2-(4-piperidinyloxy)-N-(tricyclo[3.3.1.1$^{3,7}$]dec-1-ylmethyl)-pyridine-4-carboxamide, hydrochloride salt, 5-Chloro-2-(4-piperidinylmethoxy)-N-(tricyclo[3.3.1.1$^{3,7}$]dec-1-ylmethyl)-pyridine-4-carboxamide, hydrochloride salt, 5-Chloro-2-(3-piperidinylmethoxy)-N-(tricyclo[3.3.1.1$^{3,7}$]dec-1-ylmethyl)-pyridine-4-carboxamide, hydrochloride salt, 3-Chloro-2-piperazinyl-N-(tricyclo[3.3.1.1$^{3,7}$]dec-1-ylmethyl)-pyridine-4-carboxamide, hydrochloride salt, 3-Chloro-2-(4-aminopiperidin-1-yl)-N-(tricyclo[3.3.1.1$^{3,7}$]dec-1-ylmethyl)-pyridine-4-carboxamide, hydrochloride salt, and 3-Chloro-2-(4-piperidinylmethylamino)-N-(tricyclo[3.3.1.1$^{3,7}$]dec-1-ylmethyl)-pyridine-4-carboxamide, hydrochloride salt.

The present invention further provides a process for the preparation of a compound of formula (I) as defined above which comprises:

(i) when X represents an oxygen atom or a group $O(CH_2)_{1-6}$, $O(CH_2)_{2-6}O$, $O(CH_2)_{2-3}O(CH_2)_{1-3}$, $O(CH_2)_{2-6}NR^5$ or $O(CH_2)_{2-3}NR^5(CH_2)_{1-3}$, reacting a compound of general formula

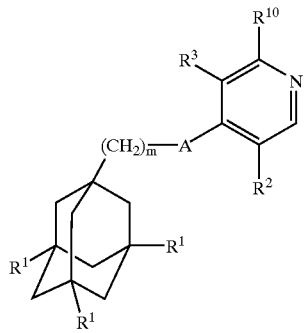

(II)

wherein $R^{10}$ represents a leaving group (e.g. a chlorine atom) and m, A, $R^1$, $R^2$ and $R^3$ are as defined in formula (I), or a compound of general formula

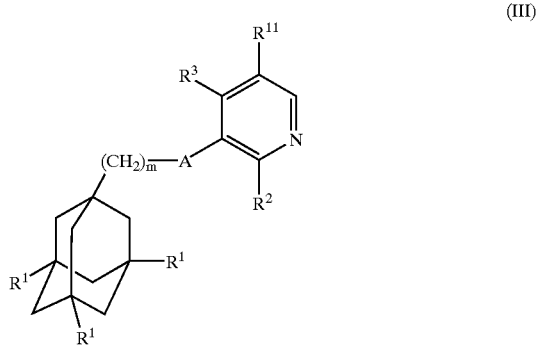

(III)

wherein $R^{11}$ represents a leaving group (e.g. a chlorine atom) and m, A, $R^1$, $R^2$ and $R^3$ are as defined in formula (I), or a compound of general formula

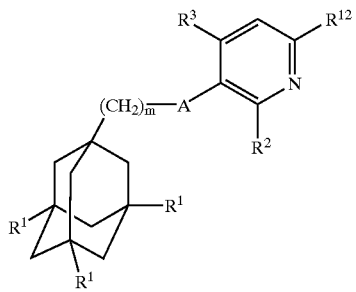

(IV)

wherein $R^{12}$ represents a leaving group (e.g. a chlorine atom) and m, A, $R^1$, $R^2$ and $R^3$ are as defined in formula (I), with a compound of general formula $$R^4\text{—}Y\text{—}OH \quad (V)$$

wherein Y represents a bond or a group $(CH_2)_{1\text{-}6}$, $O(CH_2)_{2\text{-}6}$, $(CH_2)_{1\text{-}3}O(CH_2)_{2\text{-}3}$, $NR^5(CH_2)_{2\text{-}6}$ or $(CH_2)_{1\text{-}3}NR^5(CH_2)_{2\text{-}3}$ and $R^4$ is as defined in formula (I), in the presence of a base (e.g. sodium hydride) or in the presence of a combination of a palladium catalyst (e.g. palladium acetate), a phospine ligand (e.g. BINAP) and a base (e.g. cesium carbonate); or (ii) when X represents a bond or a group $NR^5$, $NR^5(CH_2)_{1\text{-}6}$, $NR^5(CH_2)_{2\text{-}6}O$ or $NR^5(CH_2)_{2\text{-}3}O(CH_2)_{1\text{-}3}$, reacting a compound of formula (II), (III) or (IV) as defined in (i) above, with a compound of general formula $$R^4\text{—}Z \quad (VI)$$

wherein Z represents a hydrogen atom or a group $NHR^5$, $(CH_2)_{1\text{-}6}NHR^5$, $O(CH_2)_{2\text{-}6}NHR^5$ or a group $(CH_2)_{1\text{-}3}O(CH_2)_{2\text{-}3}NHR^5$ and $R^4$ and $R^5$ are as defined in formula (I), optionally in the presence of a palladium catalyst (e.g. palladium acetate), a phosphine ligand (e.g. BINAP) and a base (e.g. cesium carbonate); or (iii) when X represents a $CH_2$ group, $R^4$ represents an optionally substituted 3- to 9-membered saturated or unsaturated aliphatic heterocyclic ring system as defined in formula (I) and $R^4$ is linked to X through a nitrogen atom, reacting a compound of general formula

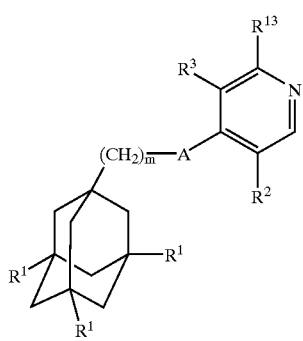

(VII)

wherein $R^{13}$ represents a group —$CH_2L^1$, $L^1$ represents a leaving group (e.g. a halogen atom) and m, A, $R^1$, $R^2$ and $R^3$ are as defined in formula (I), or a compound of general formula

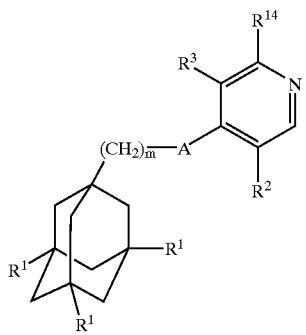

(VIII)

wherein $R^{14}$ represents a group —$CH_2L^2$, $L^2$ represents a leaving group (e.g. a halogen atom) and m, A, $R^1$, $R^2$ and $R^3$ are as defined in formula (I), or a compound of general formula

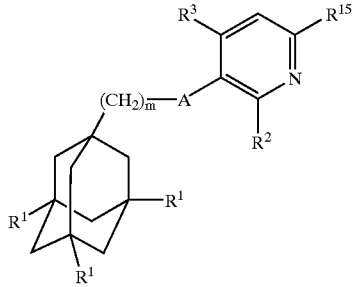

(IX)

wherein $R^{15}$ represents a group —$CH_2L^3$, $L^3$ represents a leaving group (e.g. a halogen atom) and m, A, $R^1$, $R^2$ and $R^3$ are as defined in formula (I), with a compound of general formula $$R^{4'}\text{—}H \quad (X)$$

wherein $R^{4'}$ represents an optionally substituted 3- to 9-membered saturated or unsaturated aliphatic heterocyclic ring system as defined in $R^4$ in formula (I), in the presence of a base (e.g. diisopropylethylamine); or (iv) when X represents a group $CH_2O$, reacting a compound of formula (VII), (VIII) or (IX) as defined in (iii) above with a compound of formula (V) as defined in (i) above wherein Y represents a bond, in the presence of a base (e.g. sodium hydride) or in the presence of a metal salt (e.g. silver trifluoromethanesulfonate); or (v) when X represents a group $CH_2NR^5$, reacting a compound of formula (VII), (VIII) or (IX) as defined in (iii) above with a compound of formula (VI) as defined in (ii) above wherein Z represents a group $NHR^5$; or (vi) when X represents a group CH=, reacting a compound of formula (VII), (VIII) or (IX) as defined in (iii) above with trimethyl phophite and then with a compound of general formula (XI), $R^4$=O, wherein $R^4$ is as defined in formula (I), in the presence of a base (e.g. lithium diisopropylamide); or (vii) when X represents a group $(CH_2)_{2\text{-}6}$, reacting a compound of formula (VII), (VIII) or (IX) as defined in (iii) above with trimethylphosphite and then with either a compound of general formula (XII), $R^4CHO$, wherein $R^4$ is as defined in formula (I) or with a compound of general formula (XIII), $R^4(CH_2)_{1\text{-}4}CHO$, in which $R^4$ is as defined in formula (I), in the presence of a base (e.g. lithium diisopropylamide), followed by a hydrogenation reaction (e.g. using a platinum oxide catalyst); or (viii) when X represents a group $(CH_2)_{2-6}O$, reacting a compound of formula (VII), (VIII) or (IX) as defined in (iii) above with trimethylphosphite and then with a compound of general formula (XIV), $R^4O(CH_2)_{1-4}CHO$, in which $R^4$ is as defined in formula (I), in the presence of a base (e.g. lithium diisopropylamide), followed by a hydrogenation reaction (e.g. using a platinum oxide catalyst); or (ix) when X represents a group $(CH_2)_{2-6}NR^5$, reacting a compound of formula (VII), (VIII) or (IX) as defined in (iii) above with trimethylphosphite and then with a compound of general formula (XV), $R^4NR^5(CH_2)_{1-4}CHO$, in which $R^4$ and $R^5$ are as defined in formula (I), in the presence of a base (e.g. lithium diisopropylamide), followed by a hydrogenation reaction (e.g. using a platinum oxide catalyst); or (x) when X represents a group $(CH_2)_{1-3}O(CH_2)_{1-3}$ or $(CH_2)_{1-3}O(CH_2)_{2-3}O$, reacting a compound of general formula

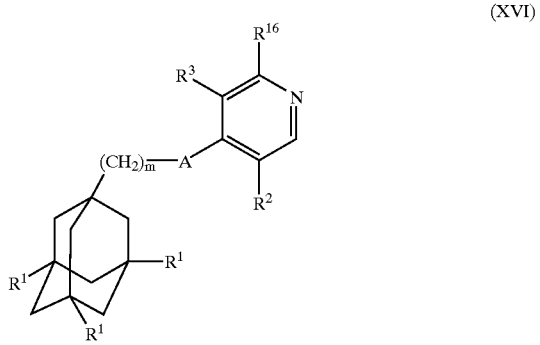

(XVI)

wherein $R^{16}$ represents a group $—(CH_2)_{1-3}L^4$, $L^4$ represents a leaving group (e.g. methanesulphonate or p-toluenesulphonate) and m, A, $R^1$, $R^2$ and $R^3$ are as defined in formula (I), or a compound of general formula

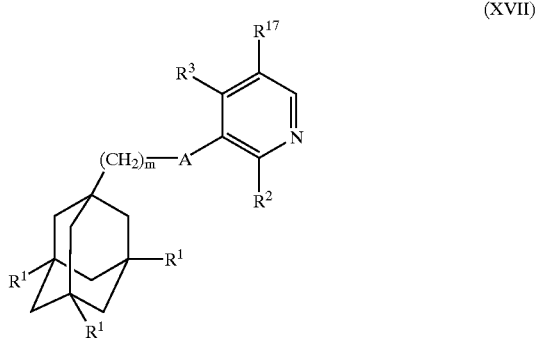

(XVII)

wherein $R^{17}$ represents a group $—(CH_2)_{1-3}L^5$, $L^5$ represents a leaving group (e.g. methanesulphonate or p-toluenesulphonate) and m, A, $R^1$, $R^2$ and $R^3$ are as defined in formula (I), or a compound of general formula

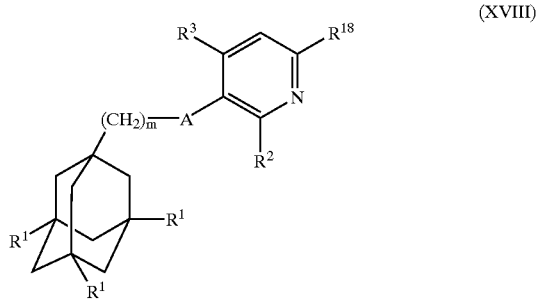

(XVIII)

wherein $R^{18}$ represents a group $—(CH_2)_{1-3}L^6$, $L^6$ represents a leaving group (e.g. methanesulphonate or p-toluenesulphonate) and m, A, $R^1$, $R^2$ and $R^3$ are as defined in formula (I),
with a compound of formula (V) as defined in (i) above wherein Y represents a group $(CH_2)_{1-3}$ or $O(CH_2)_{2-3}$, in the presence of a base (e.g. sodium hydride); or (xi) when X represents a group $(CH_2)_{1-3}NR^5(CH_2)_{1-3}$ or $(CH_2)_{1-3}NR^5(CH_2)_{2-3}O$ reacting a compound of formula (XVI), (XVII) or (XVIII) as defined in (x) above with a compound of formula (VI) as defined in (ii) above wherein Z represents a group $(CH_2)_{1-3}NHR^5$ or $O(CH_2)_{2-3}NHR^5$;

and optionally after (i), (ii), (iii), (iv), (v), (vi), (vii), (viii), (ix), (x) or (xi) converting the compound of formula (I) to a further compound of formula (I) and, if desired, forming a pharmaceutically acceptable salt or solvate of the compound of formula (I).

The processes of the invention may conveniently be carried out in a solvent, e.g. an organic solvent such as dichloromethane, dichloroethane, tetrahydrofuran, dioxane, xylene or dimethylformamide, at a temperature, e.g. in the range from 0 to 200° C., preferably in the range from 0 to 150° C.

Compounds of formula (II) in which A is NHC(O) may be prepared by reacting a compound of general formula

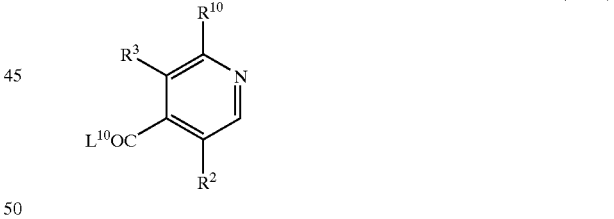

(XXX)

wherein $L^{10}$ represents a leaving group (e.g. a hydroxyl or chloride leaving group) and $R^2$, $R^3$ and $R^{10}$ are as defined in formula (II), with a compound of general formula

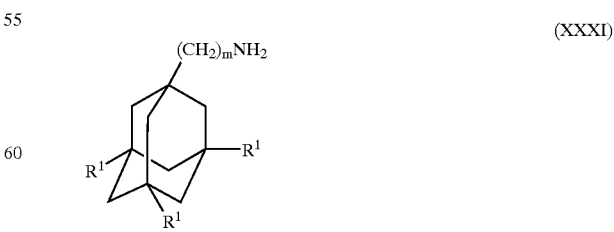

(XXXI)

wherein m and $R^1$ are as defined in formula (I), optionally in the presence of a coupling agent (e.g. 1,1'-carbonyldiimidazole).

Compounds of formulae (III), (IV), (VII), (VIII), (IX), (XVI), (XVII) and (XVIII) in which A is NHC(O) may be prepared in a similar manner to the compounds of formula (II).

Compounds of formula (II) in which A is C(O)NH may be prepared by reacting a compound of general formula

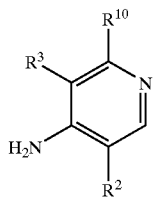
(XXXII)

wherein $R^2$, $R^3$ and $R^{10}$ are as defined in formula (II), with a compound of general formula

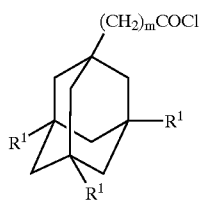
(XXXIII)

wherein m and $R^1$ are as defined in formula (I), optionally in the presence of a base (e.g. diisopropylethylamine).

Compounds of formulae (III), (IV), (VII), (VIII), (IX), (XVI), (XVII) and (XVIII) in which A is C(O)NH may be prepared in a similar manner to the compounds of formula (II).

Compounds of formulae (V), (VI), (X), (XI), (XII), (XIII), (XIV), (XV), (XXX), (XXXI), (XXXII) and (XXXIII) are either commercially available, are well known in the literature or may be prepared easily using known techniques.

Compounds of formula (I) can be converted into further compounds of formula (I) using standard procedures. For example, compounds of formula (I) in which one of $R^2$ and $R^3$ represents a nitro group can be converted to compounds of formula (I) in which one of $R^2$ and $R^3$ represents an amino group by reduction using iron powder and ammonium chloride in ethanol/water under reflux conditions. The latter compounds can in turn be converted into compounds of formula (I) in which one of $R^1$ and $R^3$ represents a halogen atom, e.g. chlorine, by diazotization (e.g. with sodium nitrite) and reaction with copper chloride. Compounds of formula (I) in which $R^6$ or $R^7$ represents a hydrogen atom can be converted to compounds of formula (I) in which $R^6$ or $R^7$ represents a $C_1$–$C_6$ alkyl, $C_2$–$C_6$ hydroxyalkyl, $C_3$–$C_8$ cycloalkyl or a 3- to 8-membered saturated heterocyclic ring by standard chemical procedures.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compounds of the present invention are advantageous in that they possess pharmacological activity. They are therefore indicated as pharmaceuticals for use in the treatment of rheumatoid arthritis, osteoarthritis, psoriasis, allergic dermatitis, asthma, chronic obstructive pulmonary disease (COPD), hyperresponsiveness of the airway, septic shock, glomerulonephritis, irritable bowel disease, Crohn's disease, ulcerative colitis, atherosclerosis, growth and metastases of malignant cells, myoblastic leukaemia, diabetes, Alzheimer's disease, meningitis, osteoporosis, bum injury, ischaemic heart disease, stroke and varicose veins.

Accordingly, the present invention provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention further provides a method of effecting immunosuppression (e.g. in the treatment of rheumatoid arthritis, irritable bowel disease, atherosclerosis or psoriasis) which comprises administering a therapeutically effective amount of a compound of formula (I), or a pharmaceutically acceptable salt or solvate thereof, as hereinbefore defined to a patient.

The invention also provides a method of treating an obstructive airways disease (e.g. asthma or COPD) which comprises administering to a patient a therapeutically effective amount of a compound of formula (I), or a pharmaceutically acceptable salt or solvate thereof, as hereinbefore defined to a patient.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Thus, the present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The present invention will now be further explained by reference to the following illustrative examples.

EXAMPLE 1

5-Chloro-2-piperazinyl-N-(tricyclo[3.3.1.1$^{3,7}$]dec-1-ylmethyl)-pyridine4-carboxamide, hydrochloride salt

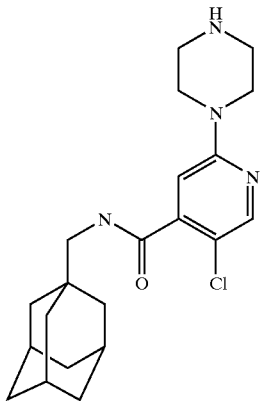

a) 2,5-Dichloro-N-(tricyclo[3.3.1.1$^{3,7}$]dec-1-ylmethyl)-pyridine-4-carboxamide To a stirred suspension of 2,5-dichlorpyridine-4-carboxylic acid (1.53 g, WO 96/33975) in dichloromethane (20 ml) and dimethylformamide (0.02 ml) at room temperature was added portionwise oxalyl chloride (3 ml). Once complete solution was achieved the mixture was stirred for a further 1 hour then concentrated in vacuo. The compound was redissolved in dichloromethane and added slowly to a solution of adamantylmethylamine in dichloromethane (20 ml) and diisopropylethylamine (2 ml). The mixture was partitioned between saturated aqueous sodium bicarbonate solution and dichloromethane and the organic layer dried over magnesium sulphate. Concentration in vacuo and crystallization (diethyl ether: isohexane) gave the sub-title compound as colourless crystals (1.62 g).

MS (APCI+ve) 339.1038 (M+H)$^+$ $^1$H NMR (DMSO-d$_6$) δ 8.59 (1H, t); 8.58 (1H, s); 7.65 (1H, s); 2.94 (2H, d); 1.94 (3H, bs); 1.7–1.57 (6H, m); 1.51 (6H, s).

b) 5-Chloro-2-piperazinyl-N-(tricyclo[3.3.1.1$^{3,7}$]dec-1-ylmethyl)-pyridine-4-carboxamide, hydrochloride salt A solution of 2,5-dichloro-N-(tricyclo[3.3.1.1$^{3,7}$]dec-1-ylmethyl)-pyridine-4-carboxamide (0.30 g, Example 1a) and 1-t-butoxycarbonylpiperazine (0.344 g) in dimethylsulfoxide (3 ml) was heated at 160° C. for 40 min. The solution was cooled and partitioned between saturated aqueous sodium bicarbonate solution and dichloromethane and the organic layer dried over magnesium sulphate. Concentration in vacuo and chromatography on silica gave a colourless solid. This was redissolved in methanol and treated with 4M HCl in dioxan (4 ml). Once deprotection was complete the solution was partially concentrated in vacuo then diluted slowly with diethyl ether with rapid stirring. The resulting white precipitate was filtered, washed with diethyl ether and dried to afford the title compound (0.195 g).

MS (APCI+ve) 389.2110 (M+H)$^+$ $^1$H NMR (DMSO-d$_6$) δ 9.43 (2H, s); 8.43 (1H, t); 8.20 (1H, s); 6.93 (1H, s); 3.77 (4H, m); 3.13 (4H, s, br); 2.93 (2H, d); 1.94 (3H, bs); 1.75–1.55 (6H, m); 1.52 (6H, s).

EXAMPLE 2

5-Chloro-2-([1,4]-diazepan-1-yl)-N-(tricyclo[3.3.1.1$^{3,7}$]dec-1-ylmethyl)-pyridine-4-carboxamide, hydrochloride salt

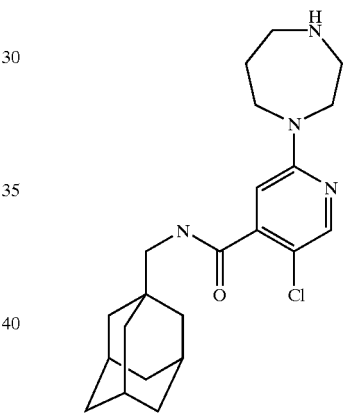

A solution of 2,5-dichloro-N-(tricyclo[3.3.1.1$^{3,7}$]dec-1-ylmethyl)-pyridine-4-carboxamide (0.50 g, Example 1a) and 1-t-butoxycarbonylhomopiperazine (0.76 g) in dimethylsulfoxide (5 ml) was heated at 100–120° C. for 24 hours. The solution was cooled and partitioned between saturated aqueous sodium bicarbonate solution and dichloromethane and the organic layer dried over magnesium sulphate. Concentration in vacuo and chromatography on silica gave a colourless solid. This was redissolved in methanol (10 ml) and treated with 4M HCl in dioxan (2 ml). Once deprotection was complete (14 hours) the solution was partially concentrated in vacuo then diluted slowly with diethyl ether with rapid stirring. The resulting white precipitate was filtered, washed with diethyl ether and dried to afford the title compound (0.51 g).

MS (APCI+ve) 403.2256 (M+H)$^+$ $^1$H NMR (DMSO-d$_6$) δ 9.23 (2H, s); 8.40 (1H, t); 8.14 (1H, s); 6.72 (1H, s); 3.92 (2H, m); 3.67 (2H, t); 3.19 (2H, m); 3.10 (2H, m); 2.93 (2H, d); 2.09 (2H, m); 1.94 (3H, m); 1.75–1.5 (6H, m); 1.52 (6H, s).

Following the procedure described in Example 1b and Example 2 the following compounds were prepared:

EXAMPLE 3

5-Chloro-2-(4-amino-piperidin-1-yl)-N-(tricyclo[3.3.1.1$^{3,7}$]dec-1-ylmethyl)-pyridine-4-carboxamide, hydrochloride salt

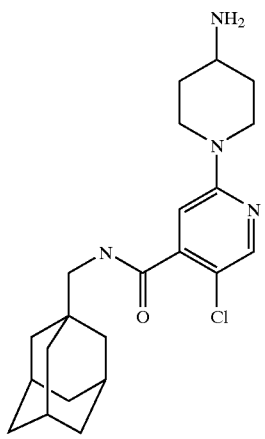

MS (APCI+ve) 403.2256 (M+H)$^+$ $^1$H NMR (DMSO-d$_6$) δ 9.23 (2H, s); 8.40 (1H, t); 8.14 (1H, s); 6.72 (1H, s); 3.92 (2H, m); 3.67 (2H, t); 3.19 (2H, m); 3.10 (2H, m); 2.93 (2H, d); 2.09 (2H, m); 1.94 (3H, m); 1.75–1.5 (6H, m); 1.52 (6H, s).

EXAMPLE 4

5-Chloro-2-(4-piperidinylmethylamino)-N-(tricyclo[3.3.1.1$^{3,7}$]dec-1-ylmethyl)-pyridine-4-carboxamide, hydrochloride salt

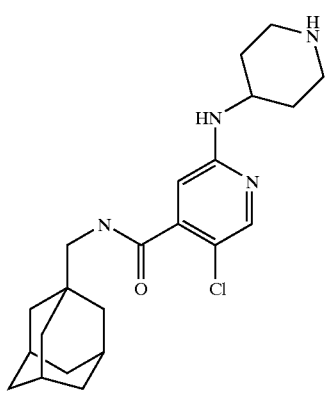

MS (APCI+ve) 403.2256 (M+H)$^+$ $^1$H NMR (DMSO-d$_6$) δ 9.23 (2H, s); 8.40 (1H, t); 8.14 (1H, s); 6.72 (1H, s); 3.92 (2H, m); 3.67 (2H, t); 3.19 (2H, m); 3.10 (2H, m); 2.93 (2H, d); 2.09 (2H, m); 1.94 (3H, m); 1.75–1.5 (6H, m); 1.52 (6H, s).

EXAMPLE 5

5-Chloro-2-(4-piperidinylmetylamino)-N-(tricyclo[3.3.1.1$^{3,7}$]dec-1-ylmethyl)-pyridine-4-carboxamide, hydrochloride salt

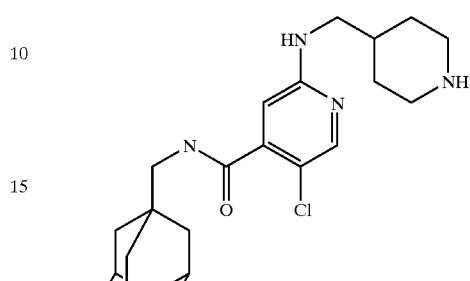

MS (APCI+ve) 417.2423 (M+H)$^+$ $^1$H NMR (DMSO-d$_6$) δ 8.82 (1H, m); 8.54 (1H, m); 8.42 (1H, t); 8.01 (1H, s); 6.59 (1H, s); 3.27–3.17 (4H, m); 2.90 (2H, d); 2.81 (2H, m); 1.94 (3H, m); 1.83 (3H, m); 1.70–1.5 (6H, m); 1.50 (6H, s); 1.34 (2H, m).

EXAMPLE 6

5-Chloro-2-(3-aminopyrrolidin-1-yl)-N-(tricyclo[3.3.1.1$^{3,7}$]dec-1-ylmethyl)-pyridine4-carboxamide, hydrochloride salt

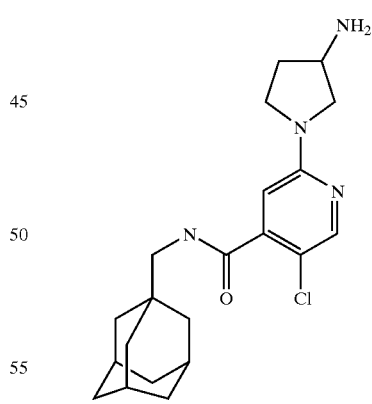

MS (APCI+ve) 438.2120 (M+H)$^+$ $^1$H NMR (DMSO-d$_6$) δ 8.43 (1H, t); 8.38 (3H, s, br); 8.14 (1H, s); 6.50 (1H, s); 3.92 (1H, m); 3.67 (1H, dd); 3.63–3.5 (2H, m); 3.46 (1H, m); 2.92 (2H, m); 2.32 (1H, m); 2.12 (1H, m); 1.94 (3H, s, br); 1.70–1.55 (6H, m); 1.50 (6H, s).

EXAMPLE 7

5-Chloro-2-(4-piperidinyloxy)-N-(tricyclo[3.3.1.1³,⁷]dec-1-ylmethyl)-pyridine-4-carboxamide, hydrochloride salt

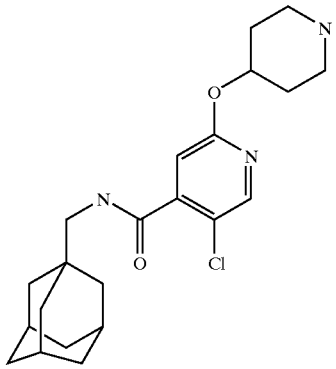

A solution of 2,5-dichloro-N-(tricyclo[3.3.1.1$^{3,7}$]dec-1-ylmethyl)-pyridine-4-carboxamide (0.30 g, Example 1a) and 1-t-butoxycarbonylpiperidine-4-ol (0.344 g) in anhydrous tetrahydrofuran (10 ml) was heated with sodium hydride (50 mg, 60% dispersion) at 70° C. for 24 hours. The solution was cooled, glacial acetic acid (0.1 ml) was added and the mixture partitioned between saturated aqueous sodium bicarbonate solution and dichloromethane. The organic layer was dried over magnesium sulphate, concentrated in vacuo and chromatographed on silica (ethyl acetate: isohexane) to give a colourless solid. This was redissolved in methanol (20 ml) and treated with 4M HCl in dioxan (4 ml). Once deprotection was complete (14 hours) the solution was partially concentrated in vacuo then diluted slowly with diethyl ether with rapid stirring. The resulting white precipitate was filtered, washed with diethyl ether and dried to afford the title compound (0.090 g).

$^{1}$H NMR (DMSO-d$_6$) δ 9.06 (2H, s, br); 8.50 (1H, t); 8.265 (1H, s); 6.88 (1H, s); 5.22 (1H, m); 3.17 (2H, m); 3.10 (2H, m); 2.93 (2H, d); 2.14 (2H, m); 1.94 (5H, m); 1.7–1.55 (6H, m); 1.55 (6H, s).

Following the procedure described in Example 7 the following compounds were prepared:

EXAMPLE 8

5-Chloro-2-(4-piperidinylmethoxy)-N-(tricyclo[3.3.1.1³,⁷]dec-1-ylmethyl)-pyridine-4-carboxamide, hydrochloride salt

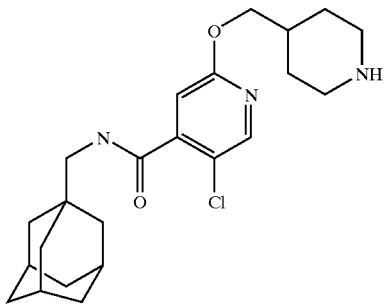

MS (APCI+ve) 418.2261 (M+1)$^+$ $^{1}$H NMR (DMSO-d$_6$) δ 8.92 (1H, m); 8.62 (1H, m); 8.50 (1H, t); 8.26 (1H, s); 6.83 (1H, s); 4.16 (2H, m+H$_2$O); 3.27 (2H, d); 2.90 (2H, d); 2.85 (2H, m); 2.07 (1H, m); 1.94 (3H, m); 1.88 (2H, d); 1.75–1.55 (6H, m); 1.58 (6H, s); 1.55–1.40 (1–2H, m).

EXAMPLE 9

5-Chloro-2-(3-piperidinylmethoxy)-N-(tricyclo[3.3.1.1³,⁷]dec-1-ylmethyl)-pyridine-4-carboxamide, hydrochloride salt

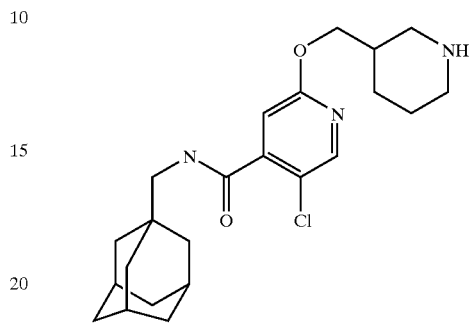

MS (APCI+ve) 418.2261 (M+H)$^+$ $^{1}$H NMR (DMSO-d$_6$) δ 9.03 (1H, m); 8.86 (1H, t); 8.51 (1H, t); 8.26 (1H, s, br); 6.87 (1H, s); 4.3–4.0 (2H, m+H$_2$O); 3.31 (1H, d); 3.22 (1H, d); 2.93 (2H, d); 2.75 (2H, m); 2.25 (1H, m); 1.94 (3H, s, br); 1.81 (2H, d); 1.70–1.58 (7H, m); 1.51 (6H, s); 1.33 (1H, m).

EXAMPLE 10

3-Chloro-2-piperazinyl-N-(tricyclo[3.3.1.1³,⁷]dec-1-ylmethyl)-pyridine-4-carboxamide, hydrochloride salt

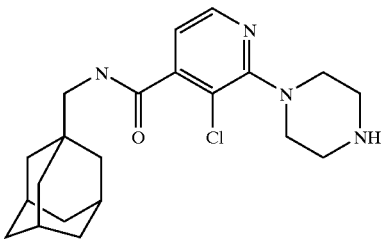

a) 2,3-Dichloro-N-(tricyclo[3.3.1.1³,⁷]dec-1-ylmethyl)-pyridine-4-carboxamide To a stirred suspension of 2,3-dichlorpyridine-4-carboxylic acid (2.1 g, WO 96/33975) in dichloromethane (100 ml) and dimethylformamide (0.03 ml) at room temperature was added portionwise oxalyl chloride (2 ml). The mixture was stirred for a further 4 hours then concentrated in vacuo. The compound was redissolved in dichloromethane and added slowly to a solution of adamantylmethylamine (2 g) in dichloromethane (20 ml) and diisopropylethylamine (3 ml) at 0° C. The mixture was partitioned between saturated aqueous sodium bicarbonate solution and dichloromethane and the organic layer dried over magnesium sulphate. Concentration in vacuo and chromatographed on silica (ethyl acetate: isohexane) gave the sub-title compound (1.28 g).

$^{1}$H NMR (DMSO-d$_6$) δ 8.59 (1H, t); 8.43 (1H, d); 7.48 (1H, d); 2.95 (2H, d); 1.99 (3H, bs); 1.7–1.6 (6H, m); 1.51 (6H, s).

b) 3-Chloro-2-piperazinyl-N-(tricyclo[3.3.1.1$^{3,7}$]dec-1-ylmethyl)-pyridine-4-carboxamide, hydrochloride salt A solution of 2,3-dichloro-N-(tricyclo[3.3.1.1$^{3,7}$]dec-1-ylmethyl)-pyridine-4-carboxamide (0.15 g, Example 10a) and 1-t-butoxycarbonylpiperazine (0.19 g) in dimethylsulfoxide (2 ml) was heated at 100° C. for 8 hours. The solution was cooled and partitioned between saturated aqueous sodium bicarbonate solution and dichloromethane and the organic layer dried over magnesium sulphate. Concentration in vacuo and chromatography on silica gave a colourless solid. This was redissolved in methanol and treated with 4M HCl in dioxan (4 ml). Once deprotection was complete the solution was partially concentrated in vacuo then diluted slowly with diethyl ether with rapid stirring. The resulting white precipitate was filtered, washed with diethyl ether and dried to afford the title compound (0.050 g).

MS (APCI+ve) 389.2122 (M+H)$^+$ $^1$H NMR (DMSO-d$_6$) δ 9.32 (2H, s, br); 8.47 (1H, t); 8.28 (1H, d); 7.07 (1H, d); 3.47 (4H, m); 3.22 (4H, s, br); 2.93 (2H, d); 1.94 (3H, s, br); 1.7–1.55 (6H, m); 1.51 (6H, s).

Following the procedure described in Example 10 the following compounds were prepared:

EXAMPLE 11

3-Chloro-2-(4-aminopiperidin-1-yl)-N-(tricyclo[3.3.1.1$^{3,7}$]dec-1-ylmethyl)-pyridine-4-carboxamide, hydrochloride salt

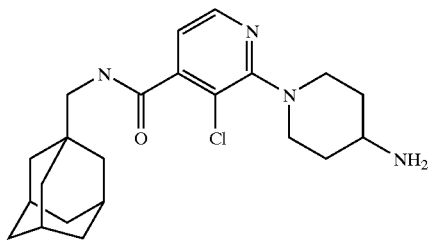

MS (APCI+ve) 403.2268 (M+H)$^+$ $^1$H NMR (DMSO-d$_6$) δ 8.45 (1H, t); 8.22 (1H, s); 8.22 (3H, s, br); 6.97 (1H, d); 3.74 (2H, d, br); 3.21 (1H, m); 2.93 (2H, d); 2.86 (2H, m); 2.02 (2H, d, br); 1.91 (3H, s, br); 1.8–1.55 (8H, m); 1.51 (6H, s).

EXAMPLE 12

3-Chloro-2-(4-piperidinylmethylamino)-N-(tricyclo[3.3.1.1$^{3,7}$]dec-1-ylmethyl)-pyridine-4-carboxamide, hydrochloride salt

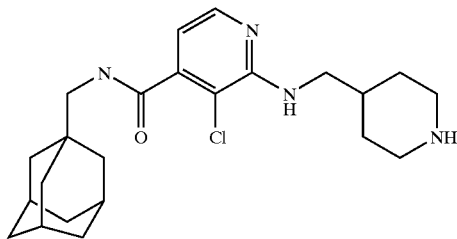

MS (APCI+ve) 417.2426 (M+H)$^+$ $^1$H NMR (DMSO-d$_6$) δ 8.90 (1H, d, br); 8.65 (1H, m); 8.42 (1H, t); 7.98 (1H, d); 7.12 (1H, s, br); 6.55 (1H, d); 3.34 (2H, s, br); 3.24 (2H, d); 2.91 (2H, d); 2.79 (2H, m); 1.94 (4H, s, br); 1.80 (2H, d, br); 1.70–1.55 (6H, m); 1.51 (6H, s); 1.37 (2H, m).

Pharmacological Analysis

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p.126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds of Examples 1 to 12 was tested for antagonist activity at the P2X$_7$ receptor. Thus, the test was performed in 96-well flat bottomed microtitre plates, the wells being filled with 250 μl of test solution comprising 200 μl of a suspension of THP-1 cells (2.5×10$^6$ cells/ml) containing 10$^{-4}$M ethidium bromide, 25 μl of a high potassium buffer solution containing 10$^{-5}$M bbATP, and 25 μl of the high potassium buffer solution containing 3×10$^{-5}$M test compound. The plate was covered with a plastics sheet and incubated at 37° C. for one hour. The plate was then read in a Perkin-Elmer fluorescent plate reader, excitation 520 nm, emission 595 nm, slit widths: Ex 15 nm, Em 20 nm. For the purposes of comparison, bbATP (a P2X$_7$ receptor agonist) and pyridoxal 5-phosphate (a P2X$_7$ receptor antagonist) were used separately in the test as controls. From the readings obtained, a pIC$_{50}$ figure was calculated for each test compound, this figure being the negative logarithm of the concentration of test compound necessary to reduce the bbATP agonist activity by 50%. Each of the compounds of Examples 1 to 12 demonstrated antagonist activity, having a pIC$_{50}$ figure>4.50.

What is claimed is:

1. A compound of formula

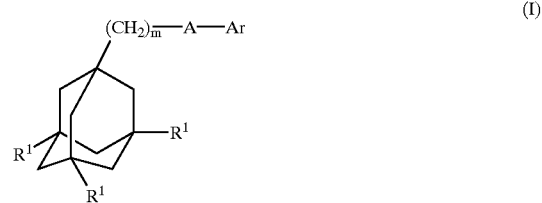

wherein m represents 1, 2 or 3;

each R$^1$ independently represents a hydrogen or halogen atom;

A represents C(O)NH or NHC(O);

Ar represents a group

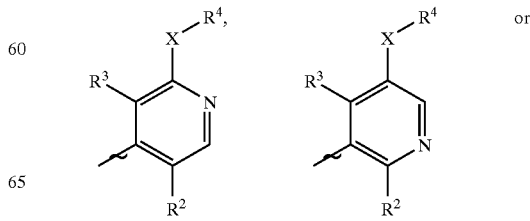

-continued

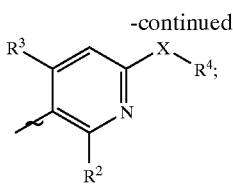

X represents a bond, an oxygen atom or a group $(CH_2)_{1-6}$, $CH=$, $(CH_2)_{1-6}O$, $O(CH_2)_{1-6}$, $O(CH_2)_{2-6}O$, $O(CH_2)_{2-3}O(CH_2)_{1-3}$, $(CH_2)_{1-3}O(CH_2)_{1-3}(CH_2)_{1-3}O(CH_2)_{2-3}O$, $NR^5$, $(CH_2)_{1-6}NR^5$, $NR^5(CH_2)_{1-6}$, $(CH_2)_{1-3}NR^5(CH_2)_{1-3}$, $O(CH_2)_{2-6}NR^5$, $O(CH_2)_{2-3}NR^5(CH_2)_{1-3}$, $(CH_2)_{1-3}NR^5(CH_2)_{2-3}O$, $NR^5(CH_2)_{2-6}O$, $NR^5(CH_2)_{2-3}O(CH_2)_{1-3}$;

one of $R^2$ and $R^3$ represents a halogen, cyano, nitro, amino, hydroxyl, or a group selected from (i) $C_1-C_6$ alkyl optionally substituted by at least one $C_3-C_6$ cycloalkyl, (ii) $C_3-C_8$ cycloalkyl, (iii) $C_1-C_6$ alkyloxy optionally substituted by at least one $C_3-C_6$ cycloalkyl, and (iv) $C_3-C_8$ cycloalkyloxy, each of these groups being optionally substituted by one or more fluorine atoms, and the other of $R^2$ and $R^3$ represents a hydrogen or halogen atom;

either $R^4$ represents a 3- to 9-membered saturated or unsaturated aliphatic heterocyclic ring system containing one or two nitrogen atoms and optionally an oxygen atom, the heterocyclic ring system being optionally substituted by one or more substituents independently selected from fluorine atoms, hydroxyl, carboxyl, cyano, $C_1-C_6$ alkyl, $C_1-C_6$ hydroxyalkyl, $-NR^6R^7$, $-(CH_2)_rNR^6R^7$ and $-CONR^6R^7$, or $R^4$ represents a 3- to 8-membered saturated carbocyclic ring system substituted by one or more substituents independently selected from $-NR^6R^7$, $-(CH_2)_rNR^6R^7$ and $-CONR^6R^7$, the ring system being optionally further substituted by one or more substituents independently selected from fluorine atoms, hydroxyl and $C_1-C_6$ alkyl;

r is 1, 2, 3, 4, 5 or 6;

$R^5$ represents a hydrogen atom or a $C_1-C_6$ alkyl or $C_3-C_8$ cycloalkyl group;

$R^6$ and $R^7$ each independently represent a hydrogen atom or a $C_1-C_6$ alkyl, $C_2-C_6$ hydroxyalkyl or $C_3-C_8$ cycloalkyl group, or $R^6$ and $R^7$ together with the nitrogen atom to which they are attached form a 3- to 8-membered saturated heterocyclic ring;

with the provisos that, (a) when A represents C(O)NH and $R^4$ represents an unsubstituted 3- to 8-membered saturated aliphatic heterocyclic ring system containing one nitrogen atom, then X is other than a bond, and (b) when A represents C(O)NH and X represents a group $(CH_2)_{1-6}$ or $O(CH_2)_{1-6}$, then $R^4$ does not represent an unsubstituted imidazolyl, unsubstituted morpholinyl, unsubstituted piperidinyl or unsubstituted pyrrolidinyl group, and (c) when A represents NHC(O) and $R^4$ represents an unsubstituted 3- to 8-membered saturated aliphatic heterocyclic ring system containing one nitrogen atom, then X is other than a bond, and (d) when A represents NHC(O) and X represents $O(CH_2)_{1-6}$ or $NH(CH_2)_{1-6}$, then $R^4$ does not represent an unsubstituted 1-piperidinyl or unsubstituted 1-pyrrolidinyl group, and (e) when A represents NHC(O) and X represents $O(CH_2)_{2-3}NH(CH_2)_2$, then $R^4$ does not represent an imidazolyl group;

or a pharmaceutically acceptable salt or solvate thereof.

2. A compound according to claim 1, wherein A represents NHC(O).

3. A compound according to claim 1, wherein Ar represents a group

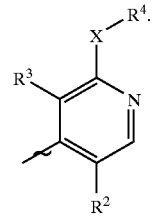

4. A compound according to claim 1, wherein X represents a bond, an oxygen atom or a group $O(CH_2)_{1-6}$, $NR^5$ or $NR^5(CH_2)_{1-6}$.

5. A compound according to claim 1, wherein $R^4$ represents a 3- to 9-membered saturated aliphatic heterocyclic ring system containing one or two nitrogen atoms and optionally an oxygen atom, the heterocyclic ring system being optionally substituted by one or two substituents independently selected from fluorine atoms, hydroxyl, carboxyl, cyano, $C_1-C_6$ alkyl, $C_1-C_6$ hydroxyalkyl, $-NR^6R^7$, $-(CH_2)_rNR^6R^7$ and $-CONR^6R^7$.

6. A compound according to claim 1, wherein $R^4$ represents a group selected from:

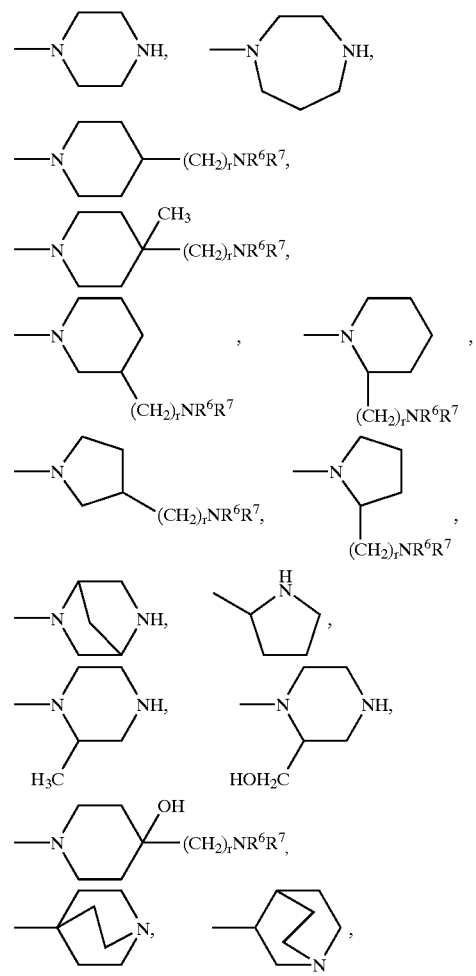

-continued

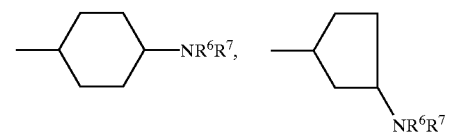
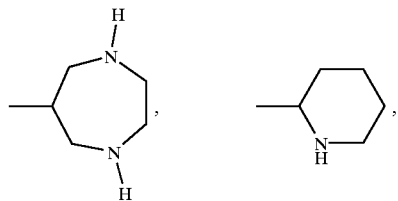
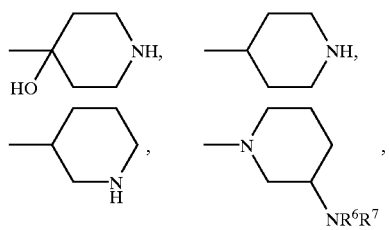
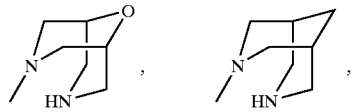
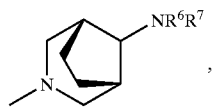
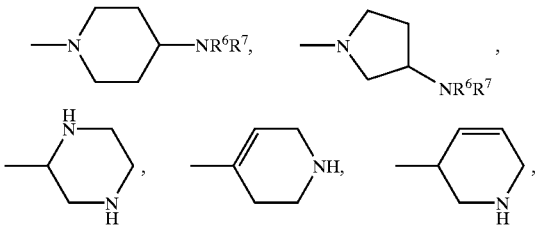
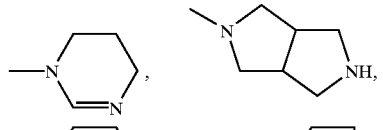
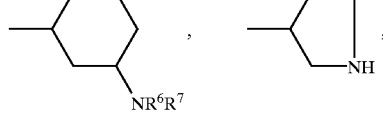
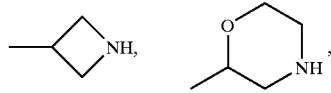
and
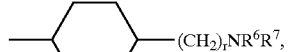
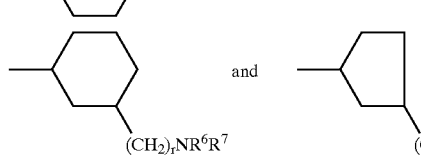

7. A compound of formula (I), or a pharmaceutically acceptable salt or solvate thereof, according to claim 1 being:

5-Chloro-2-piperazinyl-N-(tricyclo[3.3.1.1$^{3,7}$]dec-1-ylmethyl)-pyridine-4-carboxamide, hydrochloride salt, 5-Chloro-2-([1,4]-diazepan-1-yl)-N-(tricyclo[3.3.1.1$^{3,7}$]dec-1-ylmethyl)-pyridine-4-carboxamide, hydrochloride salt, 5-Chloro-2-(4-amino-piperidin-1-yl)-N-(tricyclo[3.3.1.1$^{3,7}$]dec-1-ylmethyl)-pyridine-4-carboxamide, hydrochloride salt, 5-Chloro-2-(4-piperidinylmethylamino)-N-(tricyclo[3.3.1.1$^{3,7}$]dec-1-ylmethyl)-pyridine-4-carboxamide, hydrochloride salt, 5-Chloro-2-(4-piperidinylmethylamino)-N-(tricyclo[3.3.1.1$^{3,7}$]dec-1-ylmethyl)-pyridine-4-carboxamide, hydrochloride salt, 5-Chloro-2-(3-aminopyrrolidin-1-yl)-N-(tricyclo[3.3.1.1$^{3,7}$]dec-1-ylmethyl)-pyridine-4-carboxamide, hydrochloride salt, 5-Chloro-2-(4-piperidinyloxy)-N-(tricyclo[3.3.1.1$^{3,7}$]dec-1-ylmethyl)-pyridine-4-carboxamide, hydrochloride salt, 5-Chloro-2-(4-piperidinylmethoxy)-N-(tricyclo[3.3.1.1$^{3,7}$]dec-1-ylmethyl)-pyridine-4-carboxamide, hydrochloride salt, 5-Chloro-2-(3-piperidinylmethoxy)-N-(tricyclo[3.3.1.1$^{3,7}$]dec-1-ylmethyl)-pyridine-4-carboxamide, hydrochloride salt, 3-Chloro-2-piperazinyl-N-(tricyclo[3.3.1.1$^{3,7}$]dec-1-ylmethyl)-pyridine-4-carboxamide, hydrochloride salt, 3-Chloro-2-(4-aminopiperidin-1-yl)-N-(tricyclo[3.3.1.1$^{3,7}$]dec-1-ylmethyl)-pyridine-4-carboxamide, hydrochloride salt, or 3-Chloro-2-(4-piperidinylmethylamino)-N-(tricyclo[3.3.1.1$^{3,7}$]dec-1-ylmethyl)-pyridine-4-carboxamide, hydrochloride salt.

8. A process for the preparation of a compound of formula (I) as defined in claim 1 which comprises:

(i) when X represents an oxygen atom or a group $O(CH_2)_{1-6}$, $O(CH_2)_{2-6}O$, $O(CH_2)_{2-3}O(CH_2)_{1-3}$, $O(CH_2)_{2-6}NR^5$ or $O(CH_2)_{2-3}NR^5(CH_2)_{1-3}$, reacting a compound of general formula

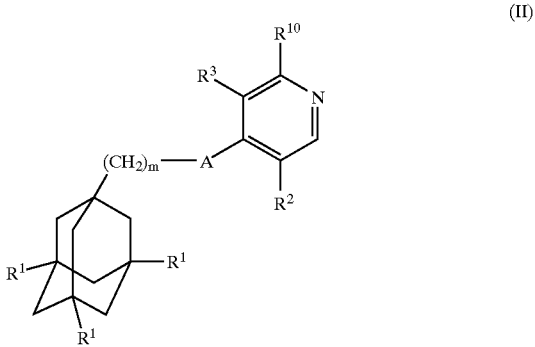

(II)

wherein $R^{10}$ represents a leaving group and m, A, $R^1$, $R^2$ and $R^3$ are as defined in formula (I), or a compound of general formula

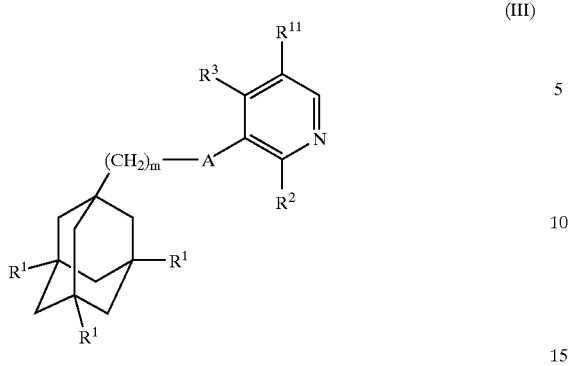
(III)

wherein $R^{11}$ represents a leaving group and m, A, $R^1$, $R^2$ and $R^3$ are as defined in formula (I), or a compound of general formula

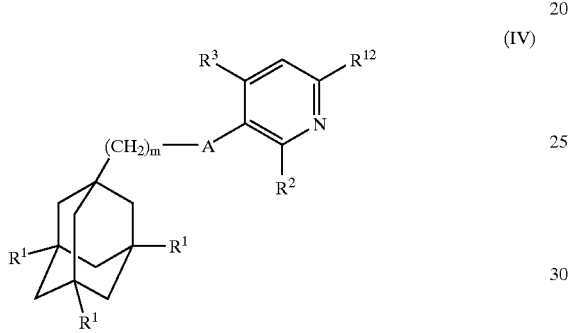
(IV)

wherein $R^{12}$ represents a leaving group and m, A, $R^1$, $R^2$ and $R^3$ are as defined in formula (I), with a compound of general formula $$R^4\text{—}Y\text{—}OH \quad (V)$$

wherein Y represents a bond or a group $(CH_2)_{1-6}$, $O(CH_2)_{2-6}$, $(CH_2)_{1-3}O(CH_2)_{2-3}$, $NR^5(CH_2)_{2-6}$ or $(CH_2)_{1-3}NR^5(CH_2)_{2-3}$ and $R^4$ is as defined in formula (I), in the presence of a base or in the presence of a combination of a palladium catalyst, a phospine ligand and a base; or (ii) when X represents a bond or a group $NR^5$, $NR^5(CH_2)_{1-6}$, $NR^5(CH_2)_{2-6}O$ or $NR^5(CH_2)_{2-3}O(CH_2)_{1-3}$, reacting a compound of formula (II), (III) or (IV) as defined in (i) above, with a compound of general formula $$R^4\text{—}Z \quad (VI)$$

wherein Z represents a hydrogen atom or a group $NHR^5$, $(CH_2)_{1-6}NHR^5$, $O(CH_2)_{2-6}NHR^5$ or a group $(CH_2)_{1-3}O(CH_2)_{2-3}NHR^5$ and $R^4$ and $R^5$ are as defined in formula (I), optionally in the presence of a palladium catalyst, a phosphine ligand and a base; or (iii) when X represents a $CH_2$ group, $R^4$ represents an optionally substituted 3- to 9-membered saturated or unsaturated aliphatic heterocyclic ring system as defined in formula (I) and $R^4$ is linked to X through a nitrogen atom, reacting a compound of general formula

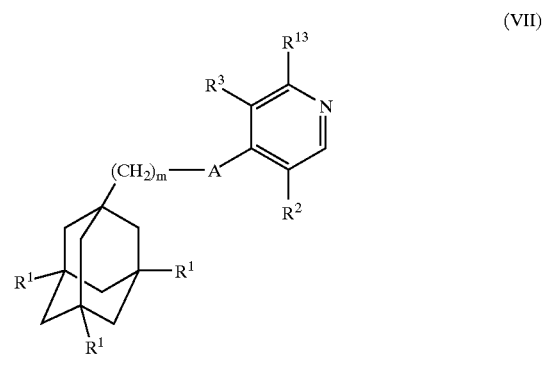
(VII)

wherein $R^{13}$ represents a group $—CH_2L^1$, $L^1$ represents a leaving group and m, A, $R^1$, $R^2$ and $R^3$ are as defined in formula (I), or a compound of general formula

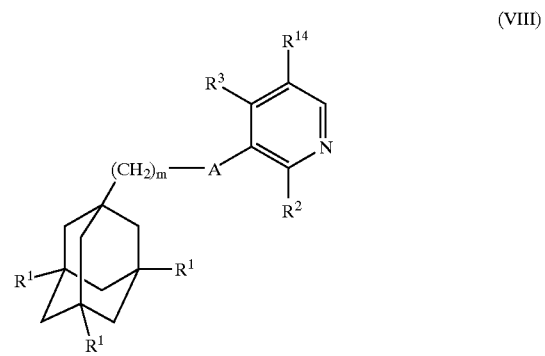
(VIII)

wherein $R^{14}$ represents a group $—CH_2L^2$, $L^2$ represents a leaving group and m, A, $R^1$, $R^2$ and $R^3$ are as defined in formula (I), or a compound of general formula

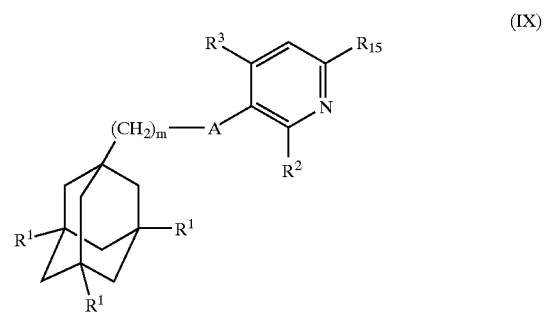
(IX)

wherein $R^{15}$ represents a group $—CH_2L^3$, $L^3$ represents a leaving group and m, A, $R^1$, $R^2$ and $R^3$ are as defined in formula (I), with a compound of general formula $$R^{4'}\text{—}H \quad (X)$$

wherein $R^{4'}$ represents an optionally substituted 3- to 9-membered saturated or unsaturated aliphatic heterocyclic ring system as defined in $R^4$ in formula (I), in the presence of a base; or (iv) when X represents a group CH₂O, reacting a compound of formula (VII), (VIII) or (IX) as defined in (iii) above with a compound of formula (V) as defined in (i) above wherein Y represents a bond, in the presence of a base or in the presence of a metal salt; or (v) when X represents a group CH₂NR⁵, reacting a compound of formula (VII), (VIII) or (IX) as defined in (iii) above with a compound of formula (VI) as defined in (ii) above wherein Z represents a group NHR⁵; or (vi) when X represents a group CH=, reacting a compound of formula (VII), (VIII) or (IX) as defined in (iii) above with trimethyl phophite and then with a compound of general formula (XI), R⁴=O, wherein R⁴ is as defined in formula (I), in the presence of a base; or (vii) when X represents a group (CH₂)₂₋₆, reacting a compound of formula (VII), (VIII) or (IX) as defined in (iii) above with trimethylphosphite and then with either a compound of general formula (XII), R⁴CHO, wherein R⁴ is as defined in formula (I) or with a compound of general formula (XIII), R⁴(CH₂)₁₋₄CHO, in which R⁴ is as defined in formula (I), in the presence of a base, followed by a hydrogenation reaction; or (viii) when X represents a group (CH₂)₂₋₆O, reacting a compound of formula (VII), (VIII) or (IX) as defined in (iii) above with trimethylphosphite and then with a compound of general formula (XIV), R⁴O(CH₂)₁₋₄CHO, in which R⁴ is as defined in formula (I), in the presence of a base, followed by a hydrogenation reaction; or (ix) when X represents a group (CH₂)₂₋₆NR⁵, reacting a compound of formula (VII), (VIII) or (IX) as defined in (iii) above with trimethylphosphite and then with a compound of general formula (XV), R⁴NR⁵(CH₂)₁₋₄CHO, in which R⁴ and R⁵ are as defined in formula (I), in the presence of a base, followed by a hydrogenation reaction; or (x) when X represents a group (CH₂)₁₋₃O(CH₂)₁₋₃ or (CH₂)₁₋₃O(CH₂)₂₋₃O, reacting a compound of general formula

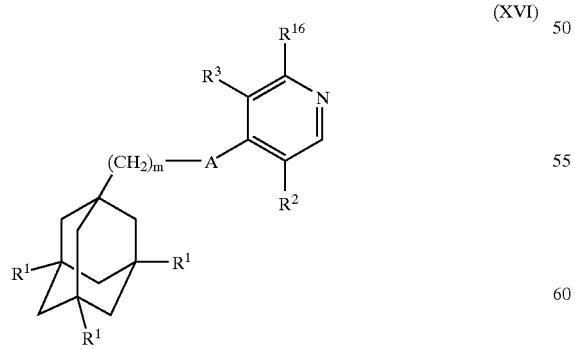

(XVI)

wherein R¹⁶ represents a group —(CH₂)₁₋₃L⁴, L⁴ represents a leaving group and m, A, R¹, R² and R³ are as defined in formula (I), or a compound of general formula

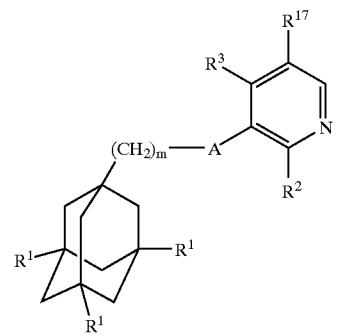

(XVII)

wherein R¹⁷ represents a group —(CH₂)₁₋₃L⁵, L⁵ represents a leaving group and m, A, R¹, R² and R³ are as defined in formula (I), or a compound of general formula

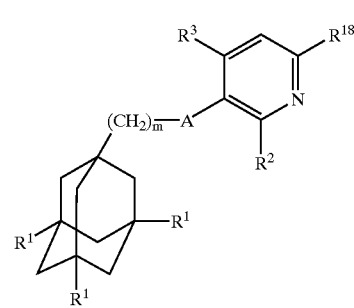

(XVIII)

wherein R¹⁸ represents a group —(CH₂)₁₋₃L⁶, L⁶ represents a leaving group and m, A, R¹, R² and R³ are as defined in formula (I), with a compound of formula (V) as defined in (i) above wherein Y represents a group (CH₂)₁₋₃ or O(CH₂)₂₋₃, in the presence of a base; or (xi) when X represents a group (CH₂)₁₋₃NR⁵(CH₂)₁₋₃ or (CH₂)₁₋₃NR⁵(CH₂)₂₋₃O reacting a compound of formula (XVI), (XVII) or (XVIII) as defined in (x) above with a compound of formula (VI) as defined in (ii) above wherein Z represents a group (CH₂)₁₋₃NHR⁵ or O(CH₂)₂₋₃NHR⁵;

and optionally after (i), (ii), (iii), (iv), (v), (vi), (vii), (viii), (ix), (x) or (xi) converting the compound of formula (I) to a further compound of formula (I) and, if desired, forming a pharmaceutically acceptable salt or solvate of the compound of formula (I).

9. A pharmaceutical composition comprising a compound of formula (I), or a pharmaceutically acceptable salt or solvate thereof, as claimed in claim 1 in association with a pharmaceutically acceptable adjuvant, diluent or carrier.

10. A process for the preparation of a pharmaceutical composition the process comprising mixing a compound of formula (I), or a pharmaceutically acceptable salt or solvate thereof, as defined in claim 1 with a pharmaceutically acceptable adjuvant, diluent or carrier.

11. A method of treating rheumatoid arthritis which comprises administering to a patient a therapeutically effective amount of a compound of formula (I), or a pharmaceutically acceptable salt or solvate thereof, as claimed in claim 1.

12. A method of treating an obstructive airways disease which comprises administering to a patient a therapeutically effective amount of a compound of formula (I), or a pharmaceutically acceptable salt or solvate thereof, as claimed in claim 1.

13. A method of treating asthma which comprises administering to a patient a therapeutically effective amount of a compound of formula (I), or a pharmaceutically acceptable salt or solvate thereof, as claimed in claim 1.

14. A method of treating chronic obstructive pulmonary disease which comprises administering to a patient a therapeutically effective amount of a compound of formula (I), or a pharmaceutically acceptable salt or solvate thereof, as claimed in claim 1.

* * * * *

UNITED STATES PATENT AND TRADEMARK OFFICE
CERTIFICATE OF CORRECTION

PATENT NO.    : 6,949,539 B2
DATED         : September 27, 2005
INVENTOR(S)   : Lilian Alcaraz and Mark Furber It is certified that error appears in the above-identified patent and that said Letters Patent is hereby corrected as shown below:

<u>Title page,</u>
Item [65], Prior Publication Data, insert -- GB 0013737.2 June 7, 2000 --.

Signed and Sealed this

Third Day of January, 2006

JON W. DUDAS
*Director of the United States Patent and Trademark Office*